(12) United States Patent
Bivolarsky et al.

(10) Patent No.: US 11,946,905 B2
(45) Date of Patent: Apr. 2, 2024

(54) EVALUATION OF FLUID QUALITY WITH SIGNALS

(71) Applicant: PERCEPTIVE SENSOR TECHNOLOGIES, INC., Tucson, AZ (US)

(72) Inventors: Lazar Bivolarsky, Cupertino, CA (US); Joel D. Burcham, Huntsville, AL (US); William Coleman, Tucson, AZ (US); James M. Heim, Tucson, AZ (US)

(73) Assignee: PERCEPTIVE SENSOR TECHNOLOGIES, INC., Tucson, AZ (US)

( * ) Notice: Subject to any disclaimer, the term of this patent is extended or adjusted under 35 U.S.C. 154(b) by 0 days.

(21) Appl. No.: 17/566,020

(22) Filed: Dec. 30, 2021

(65) Prior Publication Data

US 2022/0205951 A1    Jun. 30, 2022

Related U.S. Application Data

(60) Provisional application No. 63/132,106, filed on Dec. 30, 2020.

(51) Int. Cl.
*G01N 29/036*   (2006.01)
*G01N 29/22*    (2006.01)

(52) U.S. Cl.
CPC ......... *G01N 29/036* (2013.01); *G01N 29/222* (2013.01); *G01N 2291/02881* (2013.01)

(58) Field of Classification Search
CPC ............... G01N 29/036; G01N 29/222; G01N 2291/02881
See application file for complete search history.

(56) References Cited

U.S. PATENT DOCUMENTS

| 2,449,054 A | 9/1948 | Chantlin | 177/311 |
| 3,019,650 A | 2/1962 | Worswick | 73/290 |

(Continued)

FOREIGN PATENT DOCUMENTS

| CN | 204944617 | 1/2016 | .......... G01F 23/296 |
| CN | 105333925 | 2/2016 | .......... G01F 23/296 |

(Continued)

OTHER PUBLICATIONS

Amjad, Umar et al, "Advanced signal processing technique for damage detection in steel tubes" Proceedings of SPIE, Health Monitoring of Structural and Biological Systems 2016, 980511 (Apr. 1, 2016); 14 pgs.

(Continued)

*Primary Examiner* — Tarun Sinha
(74) *Attorney, Agent, or Firm* — HAYES SOLOWAY P.C.

(57) ABSTRACT

Systems, apparatuses, and methods for evaluation of fluid quality are provided. The system includes a vessel containing a quantity of fluid. At least one sensor is positioned to emit at least one signal into the quantity of fluid. A temperature sensor is configured to sense a temperature of the quantity of fluid. A computerized device is in communication with the at least one sensor and the temperature sensor. The processor of the computerized device calculates at least a fluid identity of the quantity of fluid and determines a quality of the quantity of fluid based on the at least one signal from the at least one sensor and the sensed temperature of the quantity of fluid. The system may have a particular benefit in evaluating dielectric fluid degradation used in liquid cooled centers and other settings.

19 Claims, 6 Drawing Sheets

(56) References Cited

U.S. PATENT DOCUMENTS

| | | | |
|---|---|---|---|
| 3,703,829 A | 11/1972 | Dougherty | 73/290 |
| 3,837,218 A | 9/1974 | Flambard et al. | G01N 29/00 |
| 3,971,962 A | 7/1976 | Green | H01L 41/08 |
| 4,065,958 A | 1/1978 | Krylova et al. | G01N 29/02 |
| 4,118,983 A | 10/1978 | Braznikov | G01F 23/28 |
| 4,121,468 A | 10/1978 | Glover et al. | G01N 29/04 |
| 4,182,177 A | 1/1980 | Prough | 73/290 |
| 4,208,908 A | 6/1980 | Hickox | G01F 1/66 |
| 4,280,126 A | 7/1981 | White | 340/621 |
| 4,320,659 A | 3/1982 | Lynnworth et al. | G01N 29/02 |
| 4,326,173 A | 4/1982 | Newman | H03L 7/08 |
| 4,501,146 A | 2/1985 | Greenhalgh | G01F 23/28 |
| 4,580,448 A | 4/1986 | Skrgatic | G01F 23/28 |
| 4,596,266 A | 6/1986 | Kinghorn et al. | B65D 88/38 |
| 4,599,892 A | 7/1986 | Doshi | G01F 17/00 |
| 4,676,098 A | 6/1987 | Erlenkämper et al. | 73/290 |
| 4,852,416 A | 8/1989 | Boone et al. | H04R 1/02 |
| 4,934,191 A | 6/1990 | Kroening et al. | 73/592 |
| 4,954,997 A | 9/1990 | Dieulesaint et al. | G08B 21/00 |
| 4,977,780 A | 12/1990 | Machida et al. | G01N 29/04 |
| 5,015,995 A | 5/1991 | Holroyd | 340/621 |
| 5,038,611 A | 8/1991 | Weldon et al. | 73/290 |
| 5,040,415 A | 8/1991 | Barkhoudarian | G01F 1/66 |
| 5,148,700 A | 9/1992 | King | G01N 15/00 |
| 5,195,058 A | 3/1993 | Simon | G01S 15/02 |
| 5,223,822 A | 6/1993 | Stommes et al. | G08B 7/06 |
| 5,295,120 A | 3/1994 | McShane | 367/188 |
| 5,325,727 A | 7/1994 | Miller et al. | G01F 1/34 |
| 5,415,033 A | 5/1995 | Maresca, Jr. et al. | 73/40.5 |
| 5,438,868 A | 8/1995 | Holden et al. | 73/290 |
| 5,453,944 A | 9/1995 | Baumoel | G06F 17/00 |
| 5,460,046 A | 10/1995 | Maltby et al. | G01N 29/24 |
| 5,469,749 A | 11/1995 | Shimada et al. | G01F 1/38 |
| 5,604,314 A | 2/1997 | Grahn | G01L 5/16 |
| 5,663,505 A | 9/1997 | Nakamura | G01L 9/0022 |
| 5,770,806 A | 6/1998 | Hiismaki | G01F 1/66 |
| 5,821,427 A | 10/1998 | Byrd | G01F 1/66 |
| 5,836,192 A | 11/1998 | Getman et al. | G01F 23/28 |
| 6,035,903 A * | 3/2000 | Few | F01M 11/0458 141/98 |
| 6,105,431 A | 8/2000 | Duffill et al. | G01N 29/2487 |
| 6,151,956 A | 11/2000 | Takahashi et al. | G01N 3/56 |
| 6,157,894 A * | 12/2000 | Hess | G01F 23/18 702/50 |
| 6,192,751 B1 | 2/2001 | Stein et al. | G08B 21/00 |
| 6,330,831 B1 | 12/2001 | Lynnworth et al. | 73/861.28 |
| 6,354,147 B1 | 3/2002 | Gysling et al. | G01N 29/00 |
| 6,368,281 B1 | 4/2002 | Solomon et al. | A61B 8/14 |
| 6,443,006 B1 * | 9/2002 | Degrave | G01F 23/266 73/304 C |
| 6,470,744 B1 | 10/2002 | Usui et al. | 73/290 |
| 6,481,287 B1 | 11/2002 | Ashworth et al. | G01K 11/24 |
| 6,513,385 B1 | 2/2003 | Han | G01N 29/00 |
| 6,575,043 B1 | 6/2003 | Huang et al. | G01F 1/66 |
| 6,578,424 B1 | 6/2003 | Ziola et al. | G01N 29/00 |
| 6,631,639 B1 | 10/2003 | Dam et al. | 73/290 |
| 6,672,163 B2 | 1/2004 | Han et al. | G01V 1/28 |
| 6,691,582 B1 | 2/2004 | Nawa et al. | G01F 1/66 |
| 6,836,734 B2 | 12/2004 | Rojas et al. | G06F 19/00 |
| 6,925,868 B2 | 8/2005 | Young et al. | 73/290 |
| 6,938,488 B2 | 9/2005 | Diaz et al. | 73/597 |
| 7,085,391 B1 | 8/2006 | Yamaya | G10H 1/00 |
| 7,114,375 B2 | 10/2006 | Panetta et al. | 73/61.75 |
| 7,246,522 B1 | 7/2007 | Diaz et al. | 73/597 |
| 7,299,136 B2 | 11/2007 | DiFoggio et al. | 702/22 |
| 7,330,797 B2 | 2/2008 | Bailey et al. | G01F 23/00 |
| 7,359,803 B2 | 4/2008 | Gysling et al. | G01N 31/00 |
| 7,363,174 B2 | 4/2008 | Kishiro et al. | G01F 25/10 |
| 7,430,924 B2 | 10/2008 | Gysling et al. | G01F 1/00 |
| 7,437,946 B2 | 10/2008 | Gysling et al. | G01F 1/22 |
| 7,624,650 B2 | 12/2009 | Gysling et al. | G01F 1/66 |
| 7,624,651 B2 | 12/2009 | Fernald et al. | G01F 1/66 |
| 7,656,747 B2 | 2/2010 | Mandal et al. | G01V 1/44 |
| 7,694,570 B1 | 4/2010 | Dam et al. | 73/644 |
| 7,757,560 B2 | 7/2010 | Hofmann | G01R 33/20 |
| 7,962,293 B2 | 6/2011 | Gysling | G01F 1/76 |
| 7,966,882 B2 | 6/2011 | Greenwood | 73/597 |
| 8,249,829 B2 * | 8/2012 | Vass | G05B 23/0254 702/179 |
| 8,346,491 B2 | 1/2013 | Loose et al. | G01F 1/00 |
| 8,482,295 B2 | 7/2013 | Sadri et al. | G01R 27/04 |
| 8,683,882 B2 | 4/2014 | Jackson | G01N 9/24 |
| 8,820,182 B2 | 9/2014 | Nikolay Nikolov et al. | H04Q 9/00 |
| 8,850,882 B2 | 10/2014 | Qu et al. | G01F 23/296 |
| 8,915,145 B1 | 12/2014 | Van Orsdol | G01F 1/74 |
| 9,057,677 B2 | 6/2015 | Field | G01N 29/032 |
| 9,383,476 B2 | 7/2016 | Trehan et al. | G01V 11/00 |
| 9,557,208 B2 | 1/2017 | Kuroda et al. | G01F 23/28 |
| 9,772,311 B2 | 9/2017 | Liljenberg et al. | G01N 29/032 |
| 9,816,848 B2 | 11/2017 | Raykhman et al. | G01F 1/86 |
| 9,835,450 B2 | 12/2017 | Deleye et al. | G01N 29/069 |
| 9,891,085 B2 | 2/2018 | Muhammad et al. | G01F 1/88 |
| 9,903,840 B2 | 2/2018 | Altpeter et al. | G01N 29/04 |
| 10,122,051 B2 | 11/2018 | Kuhne et al. | H01M 10/484 |
| 10,180,410 B2 | 1/2019 | Takahashi et al. | G01N 29/043 |
| 10,215,613 B2 | 2/2019 | Kassubek et al. | G01F 23/296 |
| 10,458,871 B2 | 10/2019 | Norli | G01L 11/04 |
| 10,794,871 B1 | 10/2020 | Blackshire et al. | G01N 29/265 |
| 11,020,793 B2 | 6/2021 | De Monte et al. | B22D 2/006 |
| 11,047,721 B2 | 6/2021 | Schöb et al. | G01F 1/66 |
| 11,274,952 B2 | 3/2022 | Bober et al. | G01F 1/66 |
| 11,293,791 B2 | 4/2022 | Firouzi et al. | G01F 1/66 |
| 11,536,696 B2 | 12/2022 | Bivolarsky et al. | G01N 29/44 |
| 11,585,690 B2 | 2/2023 | Bivolarsky et al. | G01F 23/2965 |
| 11,729,537 B2 | 8/2023 | Heim et al. | G01N 29/221 |
| 11,788,904 B2 | 10/2023 | Bivolarsky et al. | G01K 3/14 |
| 2002/0170753 A1 | 11/2002 | Clare | G01G 19/22 |
| 2002/0173230 A1 | 11/2002 | Mayes | B24B 49/00 |
| 2004/0035208 A1 | 2/2004 | Diaz et al. | G01N 29/18 |
| 2004/0079150 A1 | 4/2004 | Breed et al. | 73/291 |
| 2004/0173021 A1 | 9/2004 | Lizon et al. | 73/290 |
| 2004/0226615 A1 | 11/2004 | Morikawa et al. | G05D 7/06 |
| 2005/0055136 A1 | 3/2005 | Hofmann et al. | 700/273 |
| 2005/0102109 A1 | 5/2005 | Dubois et al. | G01B 5/28 |
| 2005/0128873 A1 | 6/2005 | LaBry | G01V 1/40 |
| 2005/0178198 A1 | 8/2005 | Freger et al. | 73/290 |
| 2005/0247070 A1 | 11/2005 | Arshansky et al. | 62/77 |
| 2006/0196224 A1 | 9/2006 | Esslinger | 62/509 |
| 2007/0001028 A1 | 1/2007 | Gysling | B05B 7/30 |
| 2007/0068248 A1 | 3/2007 | Freger | G01F 23/28 |
| 2007/0068253 A1 | 3/2007 | Carodiskey | A61B 6/00 |
| 2007/0157737 A1 | 7/2007 | Gysling et al. | G01F 1/667 |
| 2007/0205907 A1 | 9/2007 | Schenk, Jr. | G08B 21/00 |
| 2008/0092623 A1 | 4/2008 | Lynch et al. | G01N 29/02 |
| 2008/0101158 A1 * | 5/2008 | Hosseini | G01F 23/2962 367/87 |
| 2009/0007678 A1 | 1/2009 | Fukutomi et al. | G02N 29/2487 |
| 2009/0143681 A1 | 6/2009 | Jurvelin et al. | A61B 8/00 |
| 2010/0046576 A1 | 2/2010 | Desai | G01K 11/22 |
| 2010/0111133 A1 | 5/2010 | Yuhas et al. | G01K 17/00 |
| 2010/0199779 A1 | 8/2010 | Liu et al. | G01F 1/663 |
| 2010/0218599 A1 | 9/2010 | Young et al. | G01F 23/296 |
| 2010/0242593 A1 | 9/2010 | Lagergren et al. | G01F 23/296 |
| 2010/0307249 A1 | 12/2010 | Lesage et al. | G01N 29/04 |
| 2011/0029262 A1 | 2/2011 | Barkhouse | 702/55 |
| 2011/0048551 A1 | 3/2011 | Tanaka et al. | 137/486 |
| 2011/0072904 A1 | 3/2011 | Lam et al. | G01N 29/04 |
| 2011/0120218 A1 | 5/2011 | Aldridge | 73/290 |
| 2011/0239769 A1 | 10/2011 | Schmitt et al. | G01N 29/02 |
| 2011/0271769 A1 | 11/2011 | Kippersund et al. | G01F 1/66 |
| 2011/0284288 A1 | 11/2011 | Sawyer et al. | E21B 49/005 |
| 2012/0024067 A1 | 2/2012 | Oberdoerfer et al. | G01N 29/00 |
| 2012/0055239 A1 | 3/2012 | Sinha | G01N 29/00 |
| 2012/0173169 A1 | 7/2012 | Skelding | G06F 19/00 |
| 2012/0222471 A1 | 9/2012 | Raykhman et al. | G01N 29/02 |
| 2012/0226159 A1 | 9/2012 | Sinclair et al. | G01S 7/52046 |
| 2012/0259560 A1 | 10/2012 | Woltring et al. | 702/55 |
| 2012/0262472 A1 | 10/2012 | Garr et al. | G06T 11/206 |
| 2012/0265454 A1 | 10/2012 | Rudd et al. | G01F 1/66 |
| 2012/0281096 A1 | 11/2012 | Gellaboina et al. | G01S 15/89 |
| 2013/0002443 A1 | 1/2013 | Breed et al. | G08B 21/00 |
| 2013/0041597 A1 | 2/2013 | Deleye et al. | G01N 29/043 |

(56) References Cited

U.S. PATENT DOCUMENTS

| | | | |
|---|---|---|---|
| 2013/0068027 A1 | 3/2013 | Sullivan et al. | G01N 29/04 |
| 2013/0080081 A1 | 3/2013 | Dugger et al. | G01F 1/663 |
| 2013/0090575 A1 | 4/2013 | Rupp et al. | A61N 7/00 |
| 2013/0120155 A1 | 5/2013 | Hagg | G08C 19/16 |
| 2013/0128035 A1 | 5/2013 | Johns et al. | 348/135 |
| 2013/0213714 A1 | 8/2013 | Fuida | E21B 49/00 |
| 2014/0020478 A1 | 1/2014 | Ao et al. | G01F 1/66 |
| 2014/0027455 A1 | 1/2014 | Castellano et al. | B65D 88/34 |
| 2014/0076415 A1 | 3/2014 | Dunki-Jacobs et al. | E03C 1/02 |
| 2014/0107435 A1 | 4/2014 | Sharf et al. | A61B 8/00 |
| 2014/0223992 A1 | 8/2014 | Harper et al. | G01F 25/084 |
| 2014/0301902 A1 | 10/2014 | Fernald et al. | B01J 19/10 |
| 2014/0375169 A1 | 12/2014 | Na et al. | H01L 41/08 |
| 2015/0068311 A1 | 3/2015 | Tanaka et al. | G01N 17/00 |
| 2015/0075278 A1 | 3/2015 | Dockendorff et al. | G01F 23/296 |
| 2015/0177045 A1* | 6/2015 | Cobianu | G01F 23/2968 367/99 |
| 2015/0198471 A1 | 7/2015 | Furlong et al. | G01F 1/66 |
| 2015/0212045 A1 | 7/2015 | Raykhman et al. | G01F 1/74 |
| 2015/0247751 A1* | 9/2015 | Kutlik | G01F 23/2961 73/290 R |
| 2015/0260003 A1 | 9/2015 | McHugh et al. | E21B 33/076 |
| 2015/0276463 A1 | 10/2015 | Milne et al. | G01F 23/296 |
| 2015/0369647 A1 | 12/2015 | Kumar et al. | G01F 23/284 |
| 2016/0025545 A1 | 1/2016 | Saltzgiver et al. | G01F 23/263 |
| 2016/0041024 A1* | 2/2016 | Reimer | G01F 23/2962 73/290 V |
| 2016/0108730 A1 | 4/2016 | Fanini et al. | E21B 49/08 |
| 2016/0109304 A1 | 4/2016 | Yan et al. | G01K 15/00 |
| 2016/0146653 A1 | 5/2016 | Skelding | E21B 21/01 |
| 2016/0169839 A1 | 6/2016 | Gottlieb et al. | G01N 29/22 |
| 2016/0216141 A1 | 7/2016 | Leaders et al. | G01F 1/66 |
| 2016/0265954 A1 | 9/2016 | Bachmann et al. | G01F 1/667 |
| 2016/0320226 A1 | 11/2016 | Schaefer et al. | G01F 23/296 |
| 2017/0002954 A1 | 1/2017 | Brown et al. | F16K 37/0058 |
| 2017/0010144 A1 | 1/2017 | Lenner et al. | G01F 23/296 |
| 2017/0010145 A1 | 1/2017 | Lenner et al. | G01F 23/2962 |
| 2017/0010146 A1 | 1/2017 | Kassubek et al. | G01F 23/296 |
| 2017/0059389 A1 | 3/2017 | Moore et al. | G01F 23/2968 |
| 2017/0082650 A1 | 3/2017 | Hies et al. | G01F 25/0007 |
| 2017/0087526 A1 | 3/2017 | Luharuka | B01F 15/00 |
| 2017/0102095 A1 | 4/2017 | Kunita et al. | F16K 37/0091 |
| 2017/0097322 A1 | 6/2017 | Giese et al. | G01N 29/07 |
| 2017/0199295 A1 | 7/2017 | Mandal | G01V 1/50 |
| 2017/0202595 A1 | 7/2017 | Shelton, IV | A61B 18/00 |
| 2017/0239741 A1 | 8/2017 | Furuta | B23H 1/10 |
| 2017/0268915 A1 | 9/2017 | Gestner et al. | G01F 1/66 |
| 2017/0295743 A1 | 10/2017 | Brown et al. | A01J 5/0133 |
| 2017/0309989 A1 | 10/2017 | Waelde et al. | H01Q 1/225 |
| 2018/0035603 A1 | 2/2018 | Kremmer et al. | A01C 7/20 |
| 2018/0044159 A1 | 2/2018 | Crouse et al. | B67D 1/0406 |
| 2018/0080809 A1 | 3/2018 | Tokarev et al. | G01F 23/2965 |
| 2018/0113663 A1 | 4/2018 | Jain | G06F 3/14 |
| 2018/0149505 A1 | 5/2018 | Ploss et al. | G01F 1/66 |
| 2018/0266874 A1 | 9/2018 | Montoya et al. | G01F 23/68 |
| 2018/0299317 A1 | 10/2018 | Truong et al. | G01F 23/2925 |
| 2018/0306628 A1 | 10/2018 | Parrott et al. | G01F 17/00 |
| 2018/0348169 A1 | 12/2018 | Lee et al. | G01N 29/11 |
| 2019/0011304 A1 | 1/2019 | Cunningham et al. | G01F 17/00 |
| 2019/0063984 A1 | 2/2019 | Bowley | G01F 23/2962 |
| 2019/0078927 A1 | 3/2019 | Takayama et al. | G01F 23/2965 |
| 2019/0137310 A1 | 5/2019 | Xiao et al. | G01F 1/06 |
| 2019/0154480 A1 | 5/2019 | Schöb et al. | G01F 1/662 |
| 2019/0195629 A1 | 6/2019 | Vaissiere | G01C 9/00 |
| 2019/0195830 A1 | 6/2019 | Tamura et al. | G01N 29/07 |
| 2019/0272496 A1 | 9/2019 | Moeller | G06Q 10/087 |
| 2019/0368908 A1 | 12/2019 | Aughton et al. | G01F 1/66 |
| 2020/0018628 A1 | 1/2020 | Head et al. | G21C 17/022 |
| 2020/0182736 A1 | 6/2020 | Kim et al. | G01M 3/2807 |
| 2020/0195449 A1* | 6/2020 | Obaidi | H04B 11/00 |
| 2020/0200711 A1* | 6/2020 | Ferhan | G01H 3/00 |
| 2020/0378283 A1* | 12/2020 | Zhang | G01N 33/2888 |
| 2020/0378812 A1 | 12/2020 | Heim | G01F 1/667 |
| 2020/0378818 A1 | 12/2020 | Heim et al. | G01F 23/296 |
| 2021/0382014 A1 | 12/2021 | Xu et al. | G01N 29/24 |
| 2022/0034850 A1 | 2/2022 | Zhang et al. | G01N 29/22 |
| 2022/0178879 A1 | 6/2022 | Bivolarsky et al. | G02N 29/028 |
| 2022/0178881 A1 | 6/2022 | Bivolarsky et al. | G01N 29/04 |
| 2022/0276102 A1 | 9/2022 | Bivolarsky et al. | G01K 11/24 |
| 2023/0258488 A1 | 8/2023 | Coleman et al. | G01F 1/66 |

FOREIGN PATENT DOCUMENTS

| | | | |
|---|---|---|---|
| CN | 105548370 | 5/2016 | G01N 29/24 |
| DE | 10 2010 029 254 | 12/2011 | F01N 3/10 |
| EP | 0372700 | 6/1990 | G01F 23/28 |
| EP | 2450701 | 5/2012 | G01N 29/22 |
| EP | 2962096 | 2/2014 | G01N 29/07 |
| EP | 2962096 | 8/2019 | G01L 1/255 |
| GB | 2192717 | 1/1990 | G01N 29/00 |
| JP | H1073385 | 3/1998 | F28D 15/02 |
| JP | 2000314651 | 11/2000 | G01F 23/28 |
| JP | 2002340654 | 11/2002 | G01F 23/28 |
| JP | 2013140029 | 7/2013 | F01K 5/02 |
| KR | 200174618 | 3/2000 | G01N 29/24 |
| SU | WO 87/04793 | 8/1987 | G01N 29/00 |
| WO | WO 8809895 | 12/1988 | F16K 37/00 |
| WO | WO9010849 | 9/1990 | G01F 23/28 |
| WO | WO 2007/149605 | 12/2007 | |
| WO | WO2008079202 | 7/2008 | G01F 3/36 |
| WO | WO 2009/154719 | 12/2009 | G01F 17/00 |
| WO | WO 2014/021846 | 2/2014 | G01F 1/66 |
| WO | WO 2014/167471 | 10/2014 | G01F 23/30 |
| WO | WO 2020/136945 | 7/2020 | G01F 23/296 |

OTHER PUBLICATIONS

Amjad, Umar et al. "Change in time-to-flight of longitudinal (axisymmetric) wave modes due to lamination in steel pipes" Proceedings of SPIE vol. 8695, Health Monitoring of Structural and Biological Systems 2013, 869515 (Apr. 17, 2013); 10 pgs.

Amjad, Umar et al., "Effects of transducers on guided wave based structural health monitoring" Proceedings of SPIE, vol. 10600, Health Monitoring of Structural and Biological Systems XII, 106000F (Apr. 23, 2018), 10 pgs.

Amjad, U et al., "Generalized representations and universal aspects of Lamb wave dispersion relations" Proceedings of SPIE, vol. 7650, Health Monitoring of Structural and Biological Systems 2010, 76502F (Apr. 8, 2010), 9 pgs.

Amjad, Umar et al., "Detection and quantification of pipe damage from change in time of flight and phase" *Ultrasoncis* vol. 62 (2015) pp. 223-236, Jun. 11, 2015, 14 pgs.

Amjad, Umar et al., "Detection and quantification of diameter reduction due to corrosion in reinforcing steel bars" *Structural Health Monitoring* 2015, vol. 14(5) 532-543, 12 pgs.

Amjad, Umar et al., "Detection and quantification of delamination in laminated plates from the phase of appropriate guided wave modes" *Optical Engineering* 55(1), Jan. 2016, 11 pgs.

API: American Petroleum Institute Preliminary Program, Oct. 16-17, 2019, 5 pages.

Gurkov, Andrey "Gigantic Druzhba oil pipeline paralyzed for weeks" May 7, 2019, 3 pages, https://www.dw.com/en/gigantic-druzhba-oil-pipeline-paralyzed-for-weeks/a-48638989.

Hassanzadeh et al., "Investigation of factors affecting on viscosity reduction of sludge from Iranian crude oil storage tanks", Petroleum Science, vol. 15, Jul. 2018, pp. 634-643.

Kak et al., "Principles of Computerized Tomographic Imaging", IEEE, 1988, Chapter 2, 48 pgs.

Luck, Marissa "Deer Park fire a 'blemish' for the petrochemical industry's image" Houston Chronicle, Mar. 26, 2019, 3 pages https://www.houstonchronicle.com/business/energy/article/Deer-Park-fire-a-blemish-for-the-image-of-13717661.php.

Pandey, "Ultrasonic attenuation in condensed matter", Dissertation for V.B.S. Purvanchal University, 2009, Chapter 1, 36 pgs.

(56) References Cited

OTHER PUBLICATIONS

Pluta et al., "Stress Dependent Dispersion Relations of Acoustic Waves Travelling on a Chain of Point Masses Connected by Anharmonic Linear and Torsional Springs" *International Congress on Ultrasonics* AIP Conf. Proc. 1433, 471-474 (2012); 5 pgs.
Shelke, et al., "Mode-Selective Excitation and Detection of Ultrasonic Guided Waves for Delamination Detection in Laminated Aluminum Plates" IEEE Transactions on Ultrasonics, Ferroelectrics, and Frequency Control, vol. 58, No. 3, Mar. 2011, 11 pgs.
"TOPS Terminal Operating Practices Symposium" Program Agenda, Apr. 11, 2018, 1 page.
Zadler, et al., "Resonant Ultrasound Spectroscopy: theory and application", Geophysical Journal International, vol. 156, Issue 1, Jan. 2004, pp. 154-169.
Examination Report No. 1 issued in Australian Application No. 2020283140 dated Jan. 4, 2022, 6 pgs.
Examination Report No. 1 issued in Australian Patent Application No. 2020302919, dated Feb. 15, 2022, 4 pgs.
International Search Report and Written Opinion issued in PCT/US20/35404, dated Aug. 24, 2020, 11 pages.
International Search Report and Written Opinion issued in PCT/US20/39966, dated Sep. 18, 2020, 13 pages.
International Preliminary Report on Patentability issued in PCT/US20/35404 dated Nov. 16, 2021, 8 pgs.
International Preliminary Report on Patentability issued in PCT/US20/39966 dated Dec. 28, 2021, 10 pgs.
Notice of Allowance issued in U.S. Appl. No. 16/888,469, dated Dec. 23, 2020, 16 pgs.
Notice of Allowance issued in U.S. Appl. No. 17/148,122 dated Jun. 16, 2021, 8 pgs.
Notice of Allowance issued in U.S. Appl. No. 16/914,092 dated Oct. 28, 2021, 14 pgs.
Office Action issued in Canadian Patent Application No. 3,140,008, dated Feb. 14, 2022, 4 pgs.
Office Action issued in U.S. Appl. No. 16/888,469, dated Aug. 5, 2020, 8 pages.
Office Action issued in U.S. Appl. No. 16/888,469, dated Sep. 8, 2020, 20 pages.
Office Action issued in U.S. Appl. No. 16/914,092, dated Nov. 10, 2020, 22 pgs.
Office Action issued in U.S. Appl. No. 16/914,092, dated Mar. 1, 2021, 25 pgs.
Office Action issued in U.S. Appl. No. 16/914,092, dated Jun. 24, 2021, 24 pgs.
Office Action issued in U.S. Appl. No. 17/148,122, dated Mar. 2, 2021, 26 pgs.
U.S. Appl. No. 17/542,814, filed Dec. 6, 2021, Burcham.
U.S. Appl. No. 17/542,461, filed Dec. 5, 2021, Burcham.
International Search Report and Written Opinion issued in PCT/US21/61962 dated Feb. 16, 2022, 9 pgs.
International Search Report and Written Opinion issued in PCT/US21/61924 dated Feb. 16, 2022, 9 pgs.
International Search Report and Written Opinion issued in PCT/US21/62010 dated Feb. 16, 2022, 9 pgs.
International Search Report and Written Opnion issued in PCT/US21/61970 dated Feb. 18, 2022, 17 pgs.
International Search Report and Written Opinion issued in PCT/US21/61925 dated Feb. 18, 2022, 9 pgs.
International Search Report and Written Opinion issued in PCT/US21/61646 dated Feb. 25, 2022, 9 pgs.
International Search Report and Written Opinion issued in PCT/US21/65664 dated Mar. 11, 2022, 9 pgs.
International Search Report and Written Opinion issued in PCT/US21/62001 dated Mar. 9, 2022, 9 pgs.
International Search Report and Written Opinion issued in PCT/US21/61926 dated Mar. 8, 2022, 9 pgs.
Notice of Acceptance issued in Australian Application No. 2020302919 dated Mar. 2, 2022, 4 pgs.
Notice of Acceptance issued in Australian Application No. 2020283140 dated Mar. 30, 2022, 4 pgs.
Notice of Allowance issued in Canadian Application No. 3,140,008 dated May 5, 2022, 1 pg.
Office Action issued in Australian Patent Application No. 2020283140, dated Mar. 18, 2022, 5 pgs.
Office Action issued in U.S. Appl. No. 17/543,200, dated Mar. 9, 2022, 8 pages.
Office Action issued in U.S. Appl. No. 17/542,461, dated Mar. 10, 2022, 18 pages.
Office Action issued in U.S. Appl. No. 17/542,872, dated Mar. 11, 2022, 22 pages.
Office Action issued in U.S. Appl. No. 17/542,872, dated Mar. 17, 2022, 21 pages.
Office Action issued in U.S. Appl. No. 17/541,036, dated Mar. 31, 2022, 22 pages.
Office Action issued in U.S. Appl. No. 17/543,152, dated Apr. 19, 2022, 17 pages.
Office Action issued in U.S. Appl. No. 17/542,814, dated Apr. 25, 2022, 21 pages.
Vermeersch, "Influence of substrate thickness on thermal impedance of microelectronic structures", Microelectronics Reliability, 47, 2007, pp. 437-443.
Office Action issued in U.S. Appl. No. 17/542,462, dated May 27, 2022, 28 pages.
Office Action issued in U.S. Appl. No. 17/542,461, dated Jun. 27, 2022, 13 pages.
Office Action issued in U.S. Appl. No. 17/543,200, dated Jul. 20, 2022, 25 pages.
Office Action issued in U.S. Appl. No. 17/746,622, dated Jul. 22, 2022, 19 pages.
Office Action issued in U.S. Appl. No. 17/541,036, dated Aug. 9, 2022, 22 pages.
Office Action issued in U.S. Appl. No. 17/746,640, dated Aug. 18, 2022, 19 pages.
Notice of Allowance issued in U.S. Appl. No. 17/542,465, dated Jul. 11, 2022, 18 pages.
Notice of Allowance issued in U.S. Appl. No. 17/542,872, dated Jul. 11, 2022, 13 pages.
Notice of Allowance issued in U.S. Appl. No. 17/543,152, dated Jul. 29, 2022, 16 pages.
Office Action issued in U.S. Appl. No. 17/542,814, dated Aug. 26, 2022, 22 pages.
Office Action issued in U.S. Appl. No. 17/540,021, dated Sep. 15, 2022, 40 pages.
Office Action issued in U.S. Appl. No. 17/542,462, dated Nov. 14, 2022, 11 pgs.
Notice of Allowance issued in U.S. Appl. No. 17/542,461, dated Oct. 12, 2022, 9 pages.
Notice of Allowance issued in U.S. Appl. No. 17/543,200, dated Nov. 3, 2022, 16 pages.
Notice of Allowance issued in U.S. Appl. No. 17/746,622, dated Nov. 8, 2022, 16 pages.
U.S. Appl. No. 17/543,152, filed Dec. 6, 2021, Bivolarsky et al.
U.S. Appl. No. 17/542,814, filed Dec. 6, 2021, Burcham et al.
U.S. Appl. No. 17/542,461, filed Dec. 5, 2021, Burcham et al.
U.S. Appl. No. 17/542,465, filed Dec. 5, 2021, Bivolarsky et al.
U.S. Appl. No. 17/542,872, filed Dec. 6, 2021, Bivolarsky et al.
U.S. Appl. No. 17/543,200, filed Dec. 6, 2021, Bivolarsky et al.
U.S. Appl. No. 17/746,622, filed May 17, 2022, Bivolarsky et al.
Notice of Allowance issued in U.S. Appl. No. 17/540,021, dated Mar. 6, 2023, 10 pgs.
Notice of Allowance issued in U.S. Appl. No. 17/541,036, dated Mar. 31, 2023, 9 pgs.
Office Action issued in U.S. Appl. No. 17/542,462, dated Mar. 17, 2023, 11 pgs.
Office Action issued in U.S. Appl. No. 17/542,814, dated Apr. 6, 2023, 17 pgs.
Supplementary Partial EP Search Report issued in EP20 813 097.1, dated Jan. 13, 2023, 16 pgs.
International Search Report and Written Opinion issued in PCT/US23/12923 dated May 3, 2023, 9 pgs.

(56) References Cited

OTHER PUBLICATIONS

Notice of Allowance issued in U.S. Appl. No. 17/746,640, dated May 12, 2023, 15 pgs.
Office Action issued in U.S. Appl. No. 18/109,022, dated May 5, 2023, 18 pgs.
Office Action issued in U.S. Appl. No. 18/111,376, dated Jun. 15, 2023, 28 pgs.
Office Action issued in U.S. Appl. No. 17/542,814, dated Jul. 19, 2023, 25 pgs.
Supplementary European Search Report issued in EP Application No. 20 813 097.1, dated May 24, 2023, 20 pgs.
Supplementary Partial European Search Report issued in EP Application No. 20 832 739.5, dated May 25, 2023, 16 pgs.
U.S. Appl. No. 18/142,467, filed May 2, 2023, Heim et al.
U.S. Appl. No. 18/223,987, filed Jul. 19, 2023, Bivolarsky et al.
International Search Report and Written Opinion issued in PCT/US23/022505 dated Jul. 21, 2023, 9 pgs.
International Search Report and Written Opinion issued in PCT/US23/022511 dated Jul. 28, 2023, 14 pgs.
Office Action issued in U.S. Appl. No. 17/542,462, dated Sep. 6, 2023, 11 pgs.
European Search Report issued in EP Application No. 20832739.5, dated Sep. 6, 2023, 14 pgs.
U.S. Appl. No. 17/540,021, filed Dec. 1, 2021, Heim et al.
U.S. Appl. No. 17/541,036, filed Dec. 2, 2021, Heim et al.
U.S. Appl. No. 17/746,640, filed May 17, 2022, Bivolarsky et al.
U.S. Appl. No. 17/542,814, filed Dec. 6, 2021, Bivolarsky et al.
U.S. Appl. No. 18/111,376, filed Feb. 17, 2023, Bivolarsky et al.
U.S. Appl. No. 17/542,462, filed Dec. 5, 2021, Bivolarsky et al.
U.S. Appl. No. 18/109,022, filed Feb. 13, 2023, Coleman et al.
Office Action issued in U.S. Appl. No. 18/142,467, dated Dec. 6, 2023, 11 pgs.
Notice of Allowance issued in Application Serial No. 18/223,987, dated Nov. 21, 2023, 8 pgs.
Notice of Allowance issued in Application Serial No. 17/542,462, dated Jan. 8, 2024, 11 pgs.

* cited by examiner

EVALUATION OF FLUID QUALITY WITH SIGNALS

CROSS REFERENCE TO RELATED APPLICATION

This application claims benefit of U.S. Provisional Patent Application Ser. No. 63/132,106 entitled, "Evaluation of Fluid Quality" filed Dec. 30, 2020, the entire disclosure of which is incorporated herein by reference.

FIELD OF THE DISCLOSURE

The present disclosure is generally related to fluid monitoring and more particularly is related to evaluation of fluid quality.

BACKGROUND OF THE DISCLOSURE

Acoustic signals are commonly used in assessing fluids and other materials within containers, such as containers and pipelines used to store oil and gas within the petroleum industry. There are many reasons to use acoustic, or other types of waves or signals for measurements of fluids or materials in a container or other type of enclosure. For instance, some containers are not easily accessible, such as underground storage tanks and large, multi-story fuel storage containers. In another example, some containers contain fluid which requires monitoring or evaluation on a regular schedule, such that it is inefficient or impractical to conduct manual fluid evaluations.

While various sensors and devices exist for monitoring fluids within containers, many require the sensors to be within the container itself. This can be impractical since it can often be difficult to gain access to an interior of the container. Further, the material within the container can often cause degradation and malfunctions to electromechanical sensors which are submerged therein. For instance, some sensors which may be submerged within the material in the container may experience a build-up of residue or materials on certain parts thereof, such that they do not provide accurate or reliable reading.

Thus, a heretofore unaddressed need exists in the industry to address the aforementioned deficiencies and inadequacies.

SUMMARY OF THE DISCLOSURE

Embodiments of the present disclosure provide systems, apparatuses, and methods for evaluation of fluid quality. Briefly described, in architecture, one embodiment of the system, among others, can be implemented as follows. The system includes a vessel containing a quantity of fluid. At least one sensor is positioned to emit at least one signal into the quantity of fluid. A temperature sensor is configured to sense a temperature of the quantity of fluid. A computerized device is in communication with the at least one sensor and the temperature sensor, wherein a processor of the computerized device calculates at least a fluid identity of the quantity of fluid and determines a quality of the quantity of fluid based on the at least one signal from the at least one sensor and the sensed temperature of the quantity of fluid.

The present disclosure can also be viewed as providing a system for evaluation of a fluid quality of dielectric fluid. Briefly described, in architecture, one embodiment of the system, among others, can be implemented as follows. A vessel contains a quantity of dielectric fluid. At least one electronic device is submerged in the quantity of dielectric fluid. At least one sensor is positioned to emit at least one signal into the quantity of dielectric fluid. A temperature sensor is configured to sense a temperature of the quantity of dielectric fluid. A computerized device is in communication with the at least one sensor and the temperature sensor, wherein a processor of the computerized device determines a quality of the quantity of dielectric fluid based on the at least one signal from the at least one sensor and the sensed temperature of the quantity of fluid.

The present disclosure can also be viewed as providing methods of evaluating fluid quality. In this regard, one embodiment of such a method, among others, can be broadly summarized by the following steps: providing a vessel containing a quantity of fluid; positioning at least one sensor proximate to the vessel; emitting at least one signal into the quantity of fluid from the at least one sensor; sensing a temperature of the quantity of fluid with a temperature sensor; and using a processor of a computerized device in communication with the at least one sensor and the temperature sensor, calculating at least a fluid identity of the quantity of fluid and determining a quality of the quantity of fluid based on the at least one signal from the at least one sensor and the sensed temperature of the quantity of fluid.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
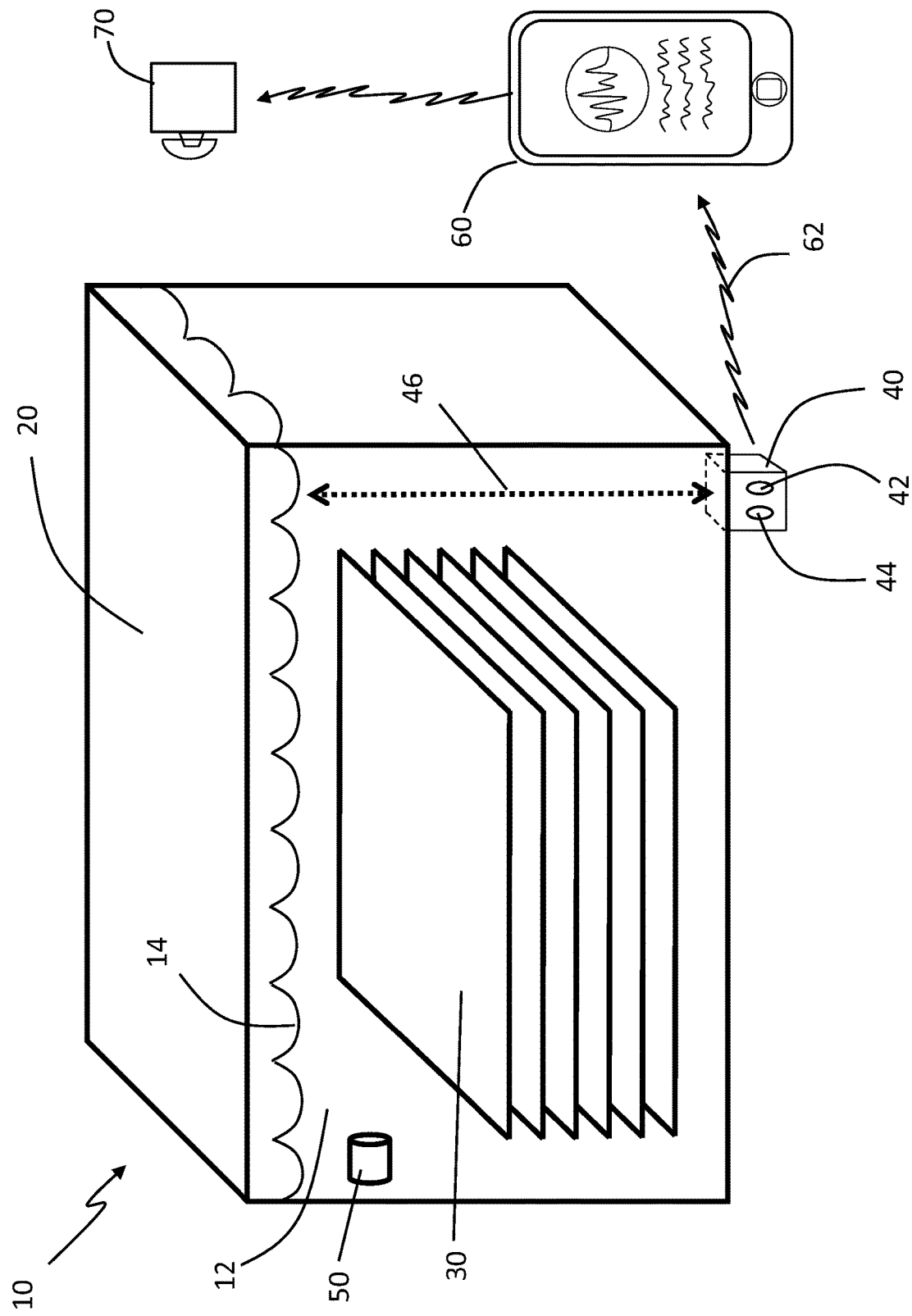
FIG. 1 is a diagrammatical illustration of a system for evaluating fluid quality, in accordance with a first exemplary embodiment of the present disclosure.

Acoustic waves or signals, and other types of waves or signals, are beneficial for use with measurements, and in particular, for measurements of fluid and other materials within metal enclosures and other acoustically transparent enclosures. In accordance with this disclosure, the fluid may include any type of liquid, gas, sludge, starch, paraffine, or similar material which continually flows or deforms when subject to a shear stress or external force. These types of enclosures may be prevalent in various commercial and industrial settings, such as processing plants, nuclear power stations, power grid transformers, and data centers, as well as in facilities that process automotive fluids, such as brake fluid and motor oil. These enclosures may include underground or buried containers, as is the case with many gas tanks, or they may be in settings where access is difficult, e.g., in a hazardous environment or at an elevated height on a tower.

In one specific example, it is common to use dielectric fluid to submerge electronics in data centers and large-scale computing environments. Dielectric fluid is an electrically non-conductive liquid that has a very high resistance to electrical breakdown. In these facilities, electronics alone, or electronics combined with mechanical components, are enclosed within containers and submerged in a dielectric fluid which is often required for the specific application in a controlled area such as a hazardous environment. For instance, with electrical equipment, dielectric fluid protects against electrical sparks or excessive heat that could ignite gasses or dust in hazardous environments. Additionally, the use of dielectric fluid may provide additional benefits, such as increasing component lifetimes by controlling temperature changes and viscosity changes within the electronics and minimizing corrosion.

However, a major risk when using dielectric fluid is quality control of the fluid, for example, to ensure it has the desired properties and is at the correct level with the vessel. If the dielectric fluid breaks down or degrades in quality, which is prone to happen over time, it can lead to inefficiencies and malfunctions with the electronics submerged therein. Additionally, if the physical level of the dielectric fluid within the vessel drops too low, it may expose the electronic components to the surrounding atmosphere, thereby leaving them prone to overheating or sparking. For instance, a leak within a vessel or container holding the dielectric fluid would, over time, reduce the amount of dielectric fluid, eventually exposing the electronics increasing heat, corrosion and risk a potential ignition in a hazardous environment. Further, not all dielectric fluids are compatible. When dielectric fluids are replaced, an incompatible mixture of the fluid can lead to accelerated degradation, which in turn, leads to reduced protection for the electronics and system parts, or even damage.

It is noted that heat generation in electronics may vary in intensity over time due to the unpredictability of the electronic processing that generate the heat. In computer datacenters, the computer hardware that is submerged in the dielectric fluid or other coolant liquid runs tasks determined by the needs of clients of that datacenter. Therefore, modeling this process is inheritable difficult, and it may be important to measure the temperature of the dielectric fluid as well as fluid quality to be able to determine degradation of the dielectric fluid cooling capabilities in real time.

Figure 2:
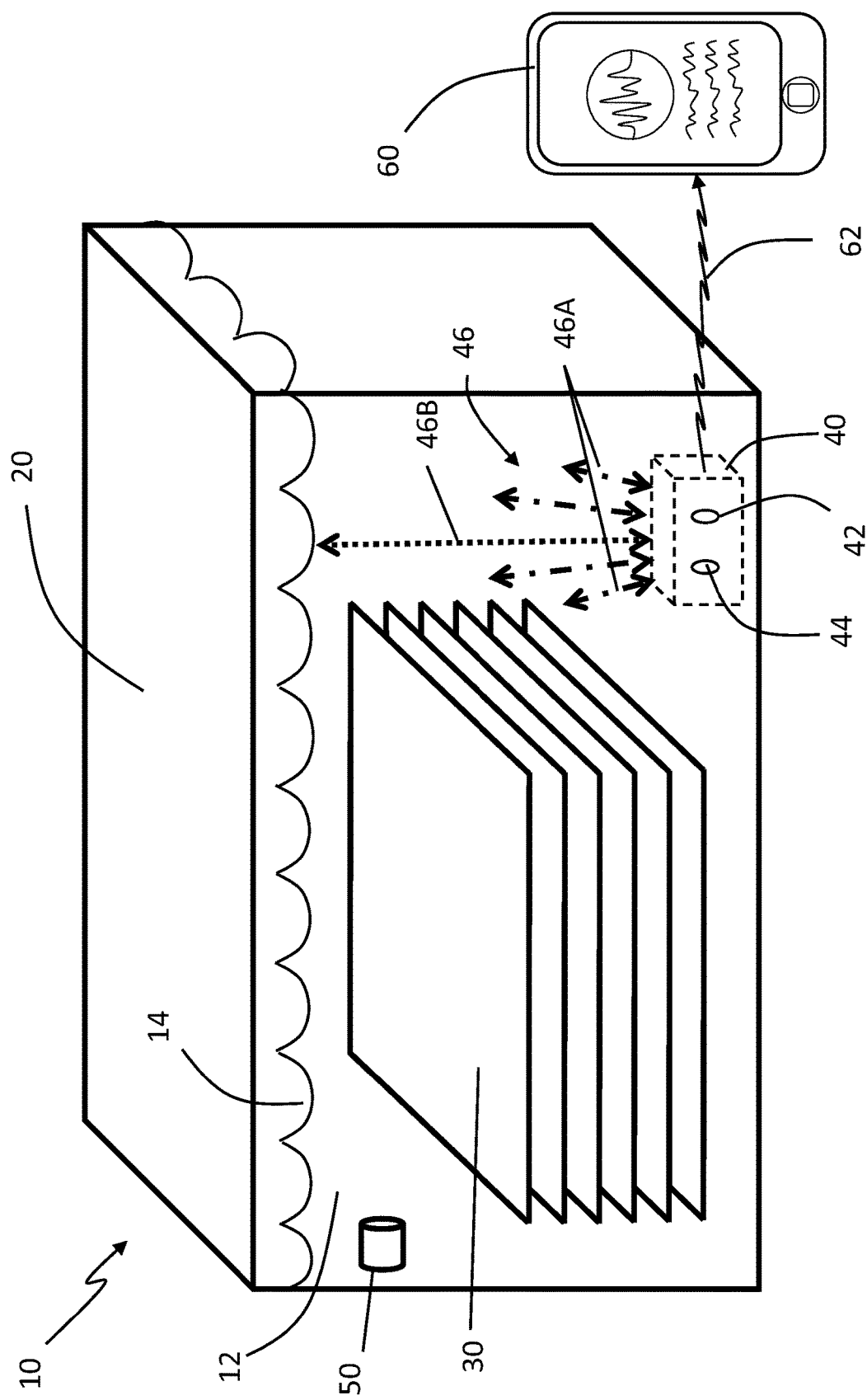
FIG. 2 is a diagrammatical illustration of the system for evaluating fluid quality, in accordance with a first exemplary embodiment of the present disclosure.
Figure 3:
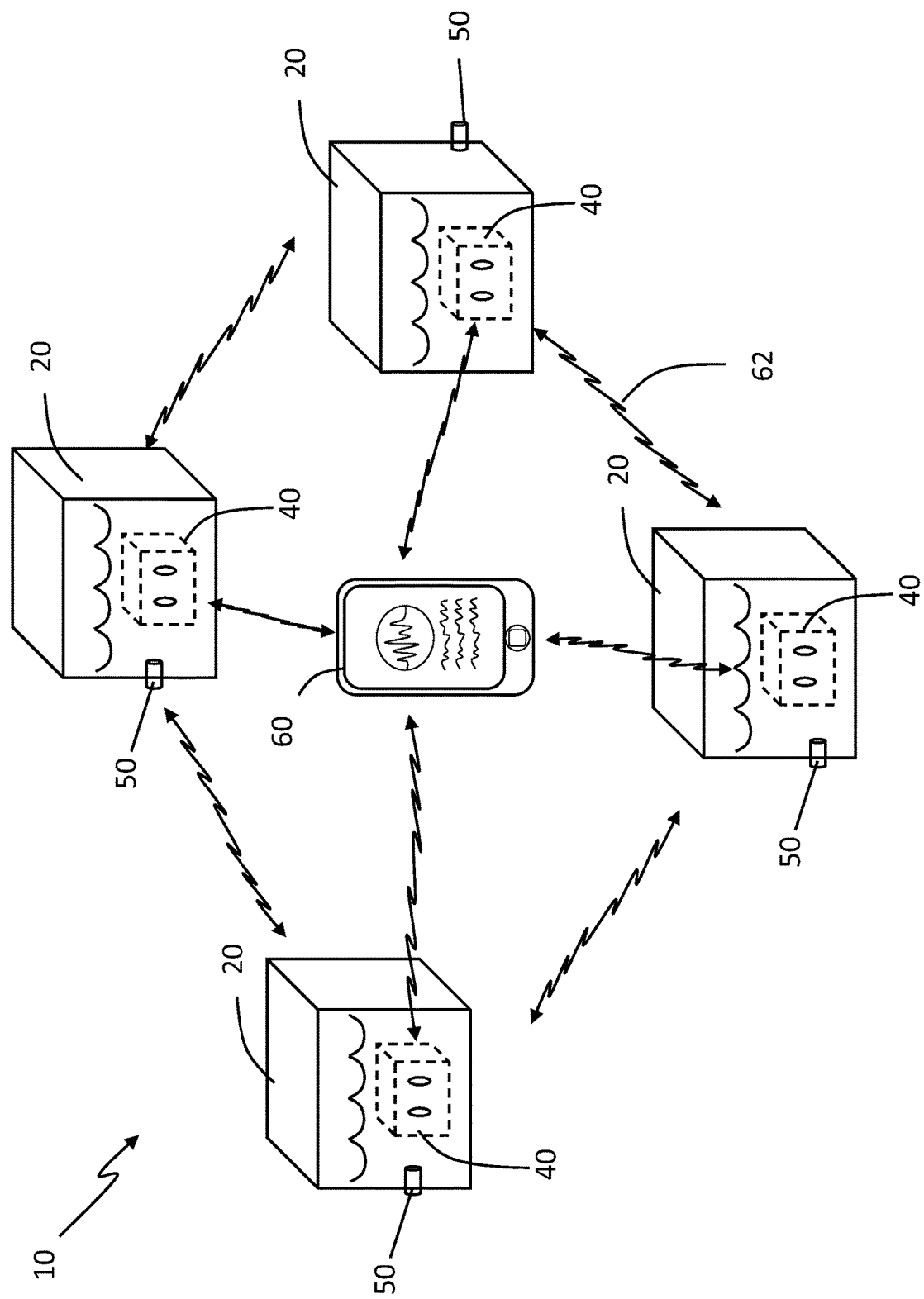
FIG. 3 is a diagrammatical illustration of a system for evaluating fluid quality having a mesh network architecture, in accordance with the first exemplary embodiment of the present disclosure.

To improve upon these issues, the subject disclosure is directed to a system for evaluating fluid quality 10. FIG. 1 is a diagrammatical illustration of a system for evaluating fluid quality 10 and FIG. 2 is a diagrammatical illustration of the system for evaluating fluid quality 10, in accordance with a first exemplary embodiment of the present disclosure. With respect to FIGS. 1-2, the system for evaluating fluid quality 10, which may be referred to herein simply as 'system 10' includes a vessel 20 containing a quantity of fluid 12. The vessel 20 may include any type of container or similar structure that is capable of holding or transporting a quantity of fluid 12 or another material. In FIGS. 1-3, the vessel 20 is depicted as a container which is holding a quantity of dielectric fluid in which electronic devices 30 are submerged. The vessel 20 may be one of many similar containers used in a liquid cooled electronics center, such as one which houses computer or network servers or the like.

At least one sensor 40 is positioned on the vessel 20 or within the vessel 20. The sensor 40 or sensors may be positioned on an exterior surface of the vessel 20, such as attached to an exterior surface of the vessel 20 sidewall or bottom, as is depicted in FIG. 1. In FIG. 2, the sensor 40 is illustrated as being positioned within the vessel 20 itself. For instance, the sensor 40 may be submerged within the fluid 12 within the vessel 20. The sensor 40 may be considered a fluid identification sensor and may include one or more of a variety of different types of sensors, commonly acoustic sensors, but other sensors, such as optical, electrical, or another type may also be used. For clarity in this disclosure, the sensor 40 is described as an acoustic sensor having one or more transducers which are capable of emitting one or more acoustic waves or signals into the fluid 12.

As shown in FIG. 1, the sensor 40 may include two transducers 42, 44 which are positioned to emit one or more acoustic signals or acoustic waves 46 into the fluid 12. In FIG. 1, the sensor 40 is depicted as emitting one acoustic wave 46 from a bottom of the vessel 20 towards a top of the vessel 20. One of the transducers 42 on the sensor 40 can identify the material identity of a fluid 12 inside the vessel 20, which in turn, is used to determine the fluid 12 quality. For example, an acoustic signal 46 is transmitted into the fluid 12 within the vessel 20 to identify that the fluid 12 in the enclosure is a dielectric fluid or another fluid material type, which can then be used to determine whether that material fluid is within an acceptable quality level. This can be achieved by the sensor 40 identifying whether the material fluid 12 detected in the vessel 20 corresponds to that of a good quality fluid or a degraded quality fluid.

In operation with a vessel 20 containing a dielectric fluid as the fluid 12, the specific fluid type may be either known or unknown. For example, the vessel 20 may be filled with a fluid 12 which is specifically known to be a certain chemical or substance, or the type of fluid 12 within the vessel 20 may be unknown. If the fluid type is unknown, the sensor 40 may be capable of accurately identifying the dielectric fluid 12. For instance, an acoustic sensor may use known acoustic metrics which are temperature-compensated against a database to identify the specific liquid type. Other types of sensors may use other metrics for determining the fluid identity.

It is noted that the acoustic wave 46 emitted from transducer 42, which is used to determine material identity, may traverse in any direction within the vessel 20, such as from the bottom to the top, from side to side, from top to bottom, diagonal, or in another other direction, or it my detect fluid parameters at a wall of the vessel 20 without traveling through the fluid. Additionally, the acoustic wave 46 may traverse through all of the fluid 12 in a cross section or directional line within the vessel 20, or through only a portion of the fluid 12. For example, as shown in FIG. 2, it is possible to have one or more signals 46A which traverse only part way through the fluid 12 with a high-frequency wave, and a second signal 46B which is emitted through substantially all of the fluid 12, e.g., from the bottom to the top of the vessel 20. The acoustic wave or waves 46A which travers only part way through the fluid 12 may allow for sensing enough properties of the fluid 12 to determine its identity without needing a clear line of sight across the vessel 20. This may be particularly beneficial for vessels 20 with many devices 30 therein, in which there is little unobstructed signal pathways across the vessel 20.

The acoustic wave 46B which traverses through a full path of the fluid 12 may be emitted by the other transducer 44, and may be used to determine a fill level or a quantity of the fluid 12 within the vessel 20. For this transducer 44, the signal 46B may traverse through the fluid 12 from a bottom surface thereof to a top surface layer 14, and reflects down to the sensor 40 such that a determination can be made on whether the fluid level has changed and/or the volume of the fluid 12 within the vessel 20. This determination results in an extremely accurate fill level measurement of the fluid 12 within the vessel.

It is noted that the sensor 40 may include any additional number of transducers which can be used to provide duplicative sensing capabilities, or to sense other aspects of the surrounding setting. For instance, the sensor 40 may use additional transducers to sense a full path of the fluid 12 in multiple directions, e.g., up and down, side to side, etc., or a transducer may be used to sense material properties of the vessel 20 itself, such as the structural condition of a vessel 20 sidewall as well as temperature profile and map the fluid degradation throughout the vessel 20. Any number of sensors 40 and transducers may be used, all of which are considered within the scope of the present disclosure.

The system 10 further includes a temperature sensor 50 which is is configured to sense a temperature of the fluid 12 within the vessel 20. It is noted that there may be multiple temperature sensors 50 sensing the temperature of the fluid at multiple locations within the vessel 20 or elsewhere. The temperature sensor 50 is shown in FIG. 1 mounted inside the vessel 20 to determine the temperature of the fluid 12, but it is noted that the temperature sensor 50 may be located inside, outside or within the vessel 20 wall, or in another position. The temperature of the fluid 12 may be taken through direct temperature measurement, e.g., from the temperature sensor 50, or from ambient temperature calculation or other techniques. All types of temperature sensors 50 can be used, including infrared temperature sensors, thermistors, other temperature sensing devices, or any combination thereof. With the type of fluid 12 material identified, any change in the fluid identity or change in the fluid level may indicate a potential problematic situation. For dielectric fluid, one potential risk is that the electronics could suffer harm or inefficiency due to degraded dielectric fluid or dielectric fluid which is below a necessary level or volume.

It is noted that the operation and functionality of the system 10 can be implemented or achieved by placing the sensors 40, 50 on an exterior wall of the vessel 20 or within an interior space or compartment of the vessel 20, such that the sensors 40, 50 are in direct contact with the fluid 12. For example, as shown in FIG. 2, the sensor 40 may be adhered to the inside of the vessel 20 or otherwise placed therein, or as shown in FIG. 1, the sensor 40 may be mounted or otherwise positioned on an outside of the vessel 20. Similarly, the temperature sensor 50 can be located inside or outside the vessel 20 in a convenient position for sensing temperature of the fluid 12. The vessel 20 does not need to be emptied or otherwise opened in order to configure the system 10 when the sensors 40, 50 are mounted outside. In other examples, the temperature sensor 50 could be positioned in other locations and would not necessarily need to be in contact with the fluid 12 or the vessel 20.

A computerized device 60 is in communication with the sensor 40 and the temperature sensor 50 with a wireless or wired communication line 62, such that a processor of the computerized device 60 is capable of receiving data and information from the sensor 40 and temperature sensor 50. This data is received by the processor which then computes or determines fluid identity of the fluid 12. For instance, using the data from the sensors 40, 50, the processor can determine that the material identity of the fluid 12 is a particular type of dielectric fluid. Based on this determination, the processor can determine a quality of the fluid 12, for instance, if the fluid 12 has suffered from any degradation or other break downs which may affect its quality. For example, any fluid degradation or contamination, or fluid additive, may result in a change in the fluid identification, such that the system 10 can differentiate between uncontaminated or non-degraded fluid and fluid which has been contaminated or has degraded. Thus, the fluid 12 can be identified in such a way that the quality of a parameter of the fluid is detectable, which in turn is used to assess the quality of the fluid 12 overall. While the system 10 can be used with a variety of fluids 12 to determine various quality parameters of the fluid, the system 10 may have a particular benefit in evaluating dielectric fluid degradation used in liquid cooled centers and other settings.

Additionally, the determination of fluid quality may be implemented through calculations completed by the computerized device 60 or another computing or processing system. To evaluate dielectric fluid 12 degradation, the processor of the computerized device 60 may determine the identity of the fluid 12 at two or more times, or at predetermined time intervals, based on at least the sensed fill level provided by fluid identity sensor 40 and the temperature from temperature sensor 50. The computerized device 60 may receive the sensed information via signals 62 from the sensors, which may be wired, wireless, or any combination thereof. The computerized device 60 may be a hand-held computing device such as a tablet computer, a smart phone, a reader, a laptop, or a stationary computing device, or any other electronic device capable of receiving the signals and calculating the data points using algorithms and processing. The computerized device 60 may include a display screen or GUI which provides relevant information to a human user, or it may be interconnected with another computing device through a network or the Internet to transfer the relevant information elsewhere.

When a determination of the fluid 12 quality or fluid quantity is made, the computerized device 60 may be in communication with an alarm 70 or warning device, as shown in FIG. 1, in order to alert personnel about the situation. This alarm 70 or warning device may include an electronic message such as an e-mail, a phone call, an audible or visual warning, or another type of alert to a control system of the facility. With this alarm, a user can take appropriate actions to correct the issue. While the type of situation which causes an alarm may change based on the type of fluid, for dielectric fluid, a chance in quality, condition, temperature, viscosity, and/or volume may cause the alarm to trigger. For example, the control system, once alerted, could execute specific actions based on the alert provided. This could include shutting down an entire facility or a unit thereof either through a specific set of shut-down steps or directly by turning off a power supply to the electronics that are submersed in the dielectric fluid. Additionally, the computerized device 60 can track the quality of fluid over a period of time and issue warnings or alerts to users of an impending issue.

It may also be possible for the computerized device 60 to perform additional assessments and/or predictive analysis based on the data received from the sensors 40, 50 and provide advance notice of anticipated situations. For example, the computerized device 60 can determine the volume of the fluid 12, or a remaining portion of the fluid 12 within the vessel 20. Using a predetermined condition based on the liquid density and identification of the fluid 12, the computerized device 60 can issue notifications to other components or parts of the system architecture. It is also possible to assess predetermined rates or patterns of flow of the fluid 12 within the vessel 20 to provide more accurate assessments, e.g., after 100 detected processing cycles for a particular fluid, the fluid is determined to be degraded. It is also possible to track the quality of the fluid 12 over a period of time, such that the quality of the fluid 12 after each cycle, each week, each month is determined.

Figure 4:
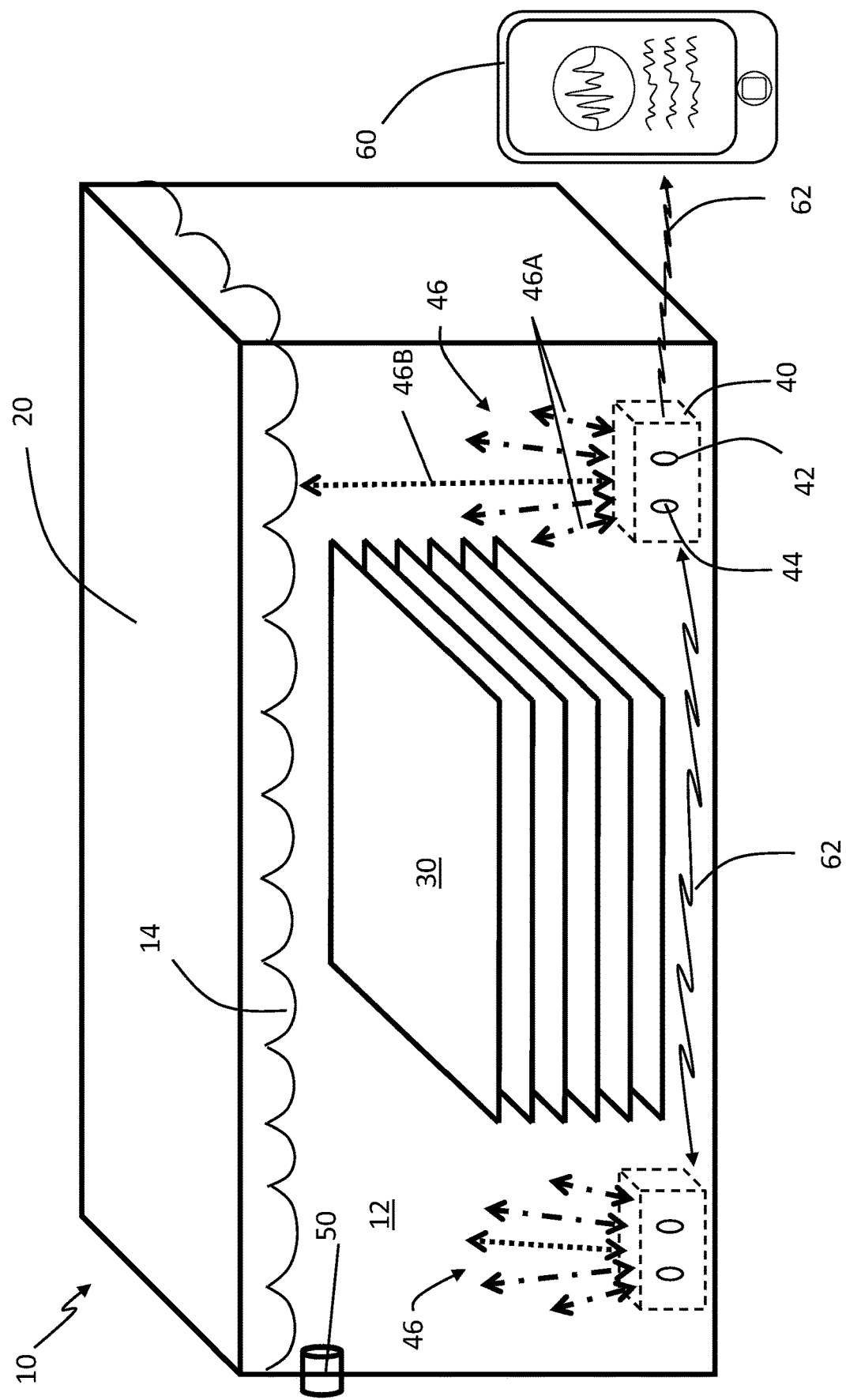
FIG. 4 is a diagrammatical illustration of a system for evaluating fluid quality having a mesh network architecture, in accordance with the first exemplary embodiment of the present disclosure.

In facilities with numerous vessels 20 or with a vessel 20 that is large, it may be possible to allow different sensors 40, 50 to communicate directly or indirectly with one another. FIG. 3 is a diagrammatical illustration of a system for evaluating fluid quality 10 having a mesh network architecture, in accordance with the first exemplary embodiment of the present disclosure. As shown in FIG. 3, a plurality of vessels 20 are provided, where the sensors 40, 50 may be formed as a mesh network where detected situations in one sensor 40 can be provided to another sensor 40 directly through one or more communication lines 62, or indirectly through a computerized device 60. In another example, FIG. 4 is a diagrammatical illustration of a system for evaluating fluid quality 10 having a mesh network architecture, in accordance with the first exemplary embodiment of the present disclosure, where a large vessel 20 may have two or more material identification sensors 40 positioned at opposing ends, and when one sensor 40 detects a change in material identity, it may communicate the change to the other sensor 40.

Figure 5:
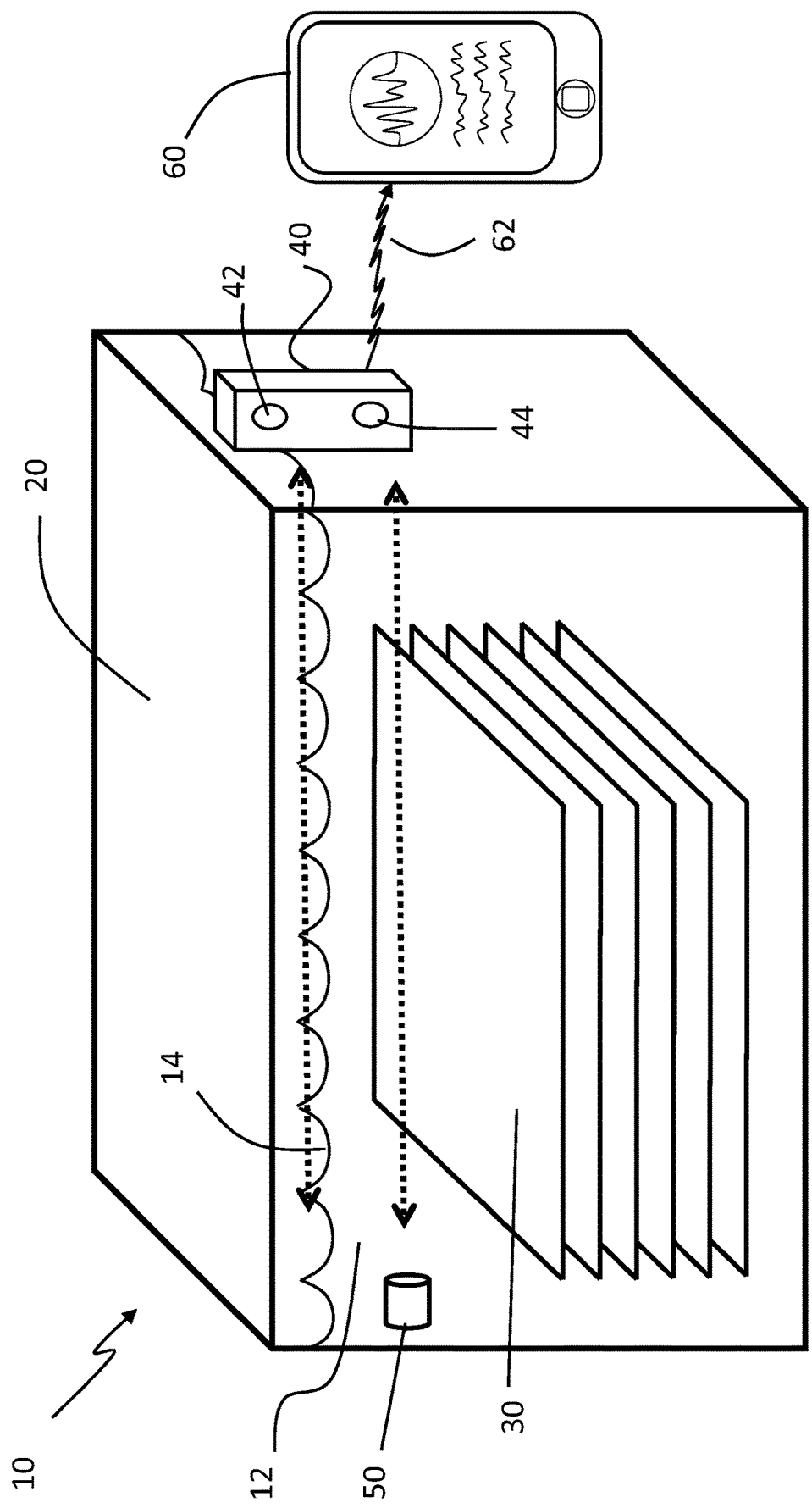
FIG. 5 is a diagrammatical illustration of a system for evaluating fluid quality, in accordance with the first exemplary embodiment of the present disclosure.

While in FIGS. 1-4, the sensor 40 is depicted as being on the bottom of the vessel 20 such that the signal 46 or signals can be transmitted upwards towards the surface 14 of the fluid 12, it is also possible to place the sensor 40 on a sidewall of the vessel 20. To this end, FIG. 5 is a diagrammatical illustration of a system for evaluating fluid quality 10, in accordance with the first exemplary embodiment of the present disclosure, in which the sensor 40 is positioned on a sidewall of the vessel 20, such that the sensor 40 can detect a fill level of the fluid 12 in the vessel 20. For example, as shown in FIG. 5, the fluid identity sensor 40 is positioned on the exterior of the vessel 20 above the fluid level that would expose the electronics 30 or other system components. While one sensor 40 with two transducers 42, 44 are depicted, any number of sensors in any positions and with any orientations may be used, all combinations of which are considered within the scope of the present disclosure. In this example, if the fluid 12 level dropped below the sensor 40, an alarm can be sounded indicating that the electronics 30 are at risk of being extricated from the fluid 12.

It may be beneficial to provide a plurality of transducers at different heights along the vessel 20, such that different warnings can be provided at different fluid 12 levels. In another example, it is possible to detect the identity of the fluid 12 without electronics 30 or other devices therein, for the purpose of identifying the quality of the fluid 12. For instance, the system 10 can be used to determine the quality of chemicals in chemical treatment baths which do not continuously have objects therein.

While it is possible to use a plurality of sensors 40, the exact number of sensors 40 may depend on the design and implementation of the system 10. For example, in some situations, it may be advantageous to utilize a single acoustic sensor 40 positioned on the bottom wall of the vessel 20, due to efficiency and lower material expense. However, for vessels 20 which do not allow access to their bottom walls, such as those sitting on the ground surface, placing sensors 40 on the sidewalls may be more beneficial. The identification sensor 40 may also be mounted at the top level of the vessel 20 to ensure that the necessary dielectric fluid is covering all of the electronics 30 inside the vessel 20. In these specific level locations, the sensor 40 identifies the appropriate dielectric fluid and determines that the fluid level in the vessel 20 is adequate to provide the required electrical protection for the devices 30.

It is also noted that given the properties of dielectric fluid inside the vessel 20 and the wall of the vessel 20 to transmit heat, as well as the flow pattern of the dielectric fluid inside the vessel 20, it may be possible for the temperature of the circuits submerged in liquid to be estimated. The flow pattern of the dielectric fluid may be predetermined, therefore more thermal sensors may need to be applied so the temperature profile inside the vessel 20 can be determined accurately. Additionally, because of the unpredictability of the heat generation by the electronics in the dielectric fluid, it may be beneficial to measure the quality of the fluid at the inside surface of the wall of the vessel 20, and then use the signal that is traversing the vessel 20 as an indicator of the internal temperature gradient.

Figure 6:
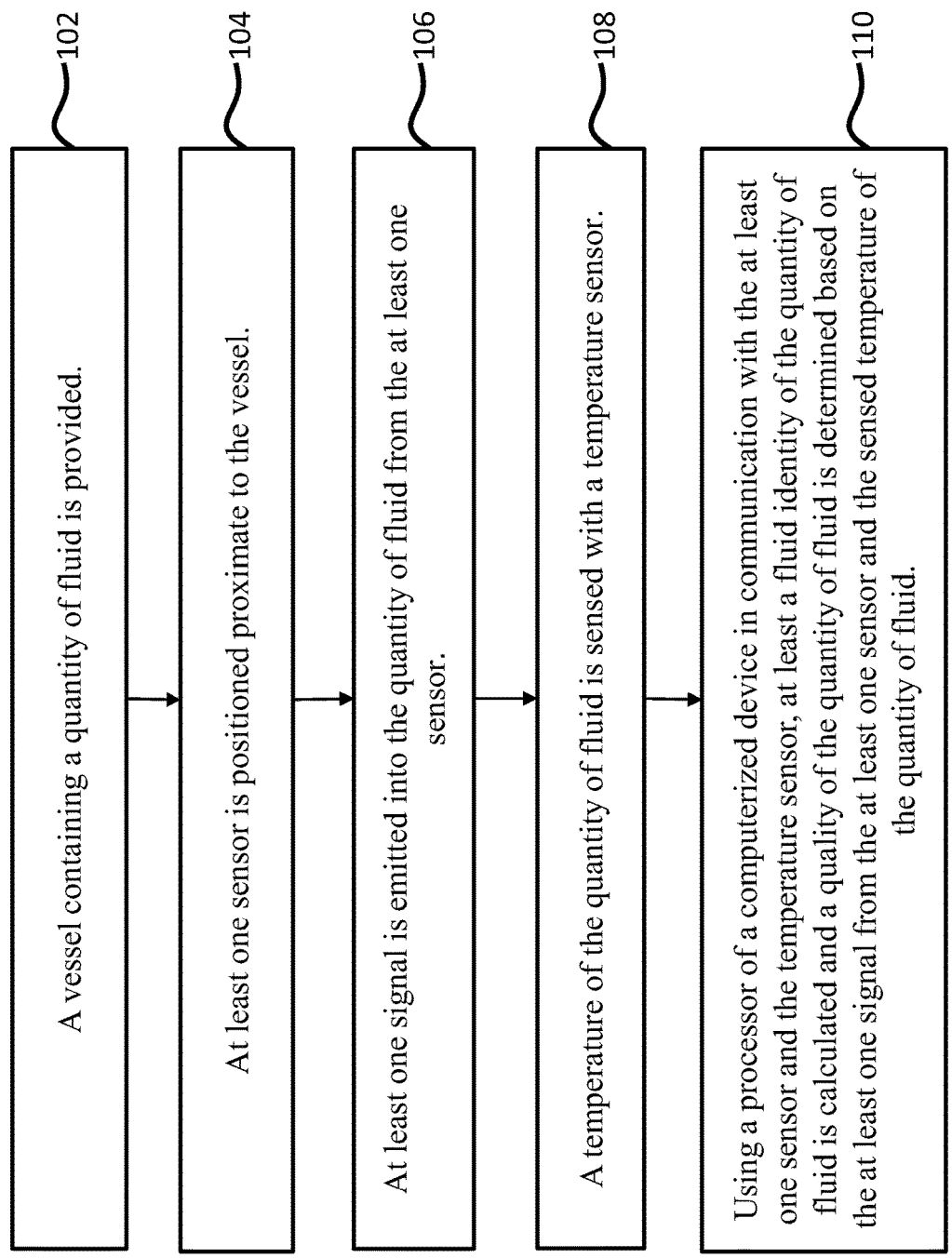
FIG. 6 is a flowchart illustrating a method of evaluating fluid quality, in accordance with the first exemplary embodiment of the disclosure.

FIG. 6 is a flowchart 100 illustrating a method of evaluating fluid quality, in accordance with the first exemplary embodiment of the disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 102, a vessel containing a quantity of fluid is provided. At least one sensor is positioned proximate to the vessel (block 104). At least one signal is emitted into the quantity of fluid from the at least one sensor (block 106). A temperature of the quantity of fluid is sensed with a temperature sensor (block 108). Using a processor of a computerized device in communication with the at least one sensor and the temperature sensor, at least a fluid identity of the quantity of fluid is calculated and a quality of the quantity of fluid is determined based on the at least one signal from the at least one sensor and the sensed temperature of the quantity of fluid (block 110). Any number of additional steps, functions, processes, or variants thereof may be included in the method, including any disclosed relative to any other figure of this disclosure.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A system for evaluation of fluid quality comprising:
   a vessel containing a quantity of fluid;
   at least two acoustic sensors positioned in at least first and second horizontal locations within an interior space of the vessel and fully submerged within the quantity of fluid, the at least two acoustic sensors positioned to emit signals into the quantity of fluid, wherein a fluid identity of the quantity of fluid in the at least first and second horizontal locations is calculatable based on the signals, wherein the at least two acoustic sensors are in direct communication with each other, and wherein the at least two acoustic sensors are configured to communicate a change in the fluid identity to one another;
   a temperature sensor configured to sense a temperature of the quantity of fluid; and
   a computerized device in communication with the at least one of the at least two acoustic sensors and the temperature sensor, wherein a processor of the computerized device determines a quality of the quantity of fluid based on the fluid identity of the quantity of fluid from the signals from the at least two acoustic sensors at two or more times and the sensed temperature of the quantity of fluid.

2. The system of claim 1, wherein the processor of the computerized device also calculates a fill level of the quantity of fluid within the vessel.

3. The system of claim 1, wherein the quantity of fluid comprises a dielectric fluid.

4. The system of claim 3, wherein the processor-determined quality of the dielectric fluid identifies a degradation of the dielectric fluid.

5. The system of claim 4, wherein the degradation of the dielectric fluid is determined at the at least first and second horizontal locations.

6. The system of claim 1, wherein each sensor of the at least two acoustic sensors is in indirect communication with each other.

7. The system of claim 1, wherein each acoustic sensor is configured to emit its own signals.

8. The system of claim 1, wherein the processor of the computerized device determines a flow of the quantity of fluid within the vessel based on the fluid identity of the quantity of fluid calculated at the first and second horizontal locations.

9. A system for evaluation of a fluid quality of dielectric fluid, the system comprising:
   at least two vessels, each containing a quantity of dielectric fluid;
   at least one electronic device submerged in the quantity of dielectric fluid of each vessel;
   at least two acoustic sensors positioned in at least first and second horizontal locations within an interior space of each vessel and fully submerged within the quantity of fluid, the at least two acoustic sensors positioned to emit at least one signal into the quantity of dielectric fluid of each vessel, each acoustic sensor configured to emit its own signals;
   a temperature sensor configured to sense a temperature of the quantity of dielectric fluid of each vessel; and
   a computerized device in communication with at least one of the at least two acoustic sensors and at least one of the temperature sensors, wherein a processor of the computerized device determines a quality of the quantity of dielectric fluid in at least one vessel based on the signals from the at least two acoustic sensors and the sensed temperature of the quantity of fluid of that vessel, wherein the at least one of the at least two acoustic sensors of each vessel is in direct communication with another sensor.

10. The system of claim 9, wherein the processor of the computerized device also calculates a fill level of the quantity of dielectric fluid within the vessel.

11. The system of claim 9, wherein the processor-determined quality of the dielectric fluid identifies a degradation of the quantity of dielectric fluid.

12. The system of claim 9, wherein a fluid identity of the quantity of fluid at the first and second horizontal locations in each vessel is calculatable based on the signals, wherein the at least two acoustic sensors in each vessel are in direct communication with each other, and wherein the at least two acoustic sensors are configured to communicate a change in the fluid identity to one another.

13. The system of claim 9, wherein the at least first and second horizontal locations are separated by the at least one electronic device.

14. A method of evaluating fluid quality, the method comprising:
   providing a vessel containing a quantity of fluid;
   positioning at least two acoustic sensors in at least first and second horizontal locations within an interior space of the vessel and fully submerged within the quantity of fluid, wherein the at least two sensors are in direct communication with each other;
   emitting signals into the quantity of fluid from the at least two acoustic sensors, wherein a fluid identity of the quantity of fluid in the at least first and second horizontal locations is calculatable based on the signals, and wherein the at least two acoustic sensors are configured to communicate a change in the fluid identity to one another;
   sensing a temperature of the quantity of fluid with a temperature sensor; and
   using a processor of a computerized device in communication with at least one of the at least two acoustic sensors and the temperature sensor, determining a quality of the quantity of fluid based on the fluid identity of the quantity of fluid from the signals from the at least two acoustic sensors at two or more times and the sensed temperature of the quantity of fluid.

15. The method of claim 14, further comprising calculating, with the processor of the computerized device, a fill level of the quantity of fluid within the vessel.

16. The method of claim 14, wherein the quantity of fluid comprises a dielectric fluid.

17. The method of claim 16, further comprising identifying a degradation of the dielectric fluid.

18. The method of claim 14, wherein the at least two acoustic sensors are in indirect communication with each other.

19. The method of claim 14, wherein each acoustic sensor is configured to emit its own signals.

* * * * *